United States Patent
Matsumura et al.

(10) Patent No.: US 8,137,643 B2
(45) Date of Patent: Mar. 20, 2012

(54) MICROPLATE MOUNTING STAND, AND ANALYTE TESTING/OBSERVING APPARATUS EQUIPPED THEREWITH

(75) Inventors: Kazuyuki Matsumura, Tokyo (JP); Shuichi Akiyama, Kasukabe (JP)

(73) Assignee: Hirata Corporation (JP)

( * ) Notice: Subject to any disclaimer, the term of this patent is extended or adjusted under 35 U.S.C. 154(b) by 333 days.

(21) Appl. No.: 12/227,021

(22) PCT Filed: May 22, 2006

(86) PCT No.: PCT/JP2006/310112
§ 371 (c)(1),
(2), (4) Date: Apr. 1, 2009

(87) PCT Pub. No.: WO2007/129413
PCT Pub. Date: Nov. 15, 2007

(65) Prior Publication Data
US 2010/0054993 A1  Mar. 4, 2010

(30) Foreign Application Priority Data
May 9, 2006  (JP) .................. 2006-130867

(51) Int. Cl.
*B01L 99/00* (2010.01)
(52) U.S. Cl. ........ 422/569; 422/561; 422/551; 422/552; 422/553

(58) Field of Classification Search .................. 422/102, 422/104, 99, 100, 561, 569, 503, 528, 547, 422/552, 553
See application file for complete search history.

(56) References Cited

U.S. PATENT DOCUMENTS

| | | | |
|---|---|---|---|
| 3,650,306 A * | 3/1972 | Lancaster | 141/238 |
| 4,257,868 A | 3/1981 | Arima et al. | 204/299 |
| 5,147,610 A | 9/1992 | Watanabe et al. | 422/64 |
| 2003/0180191 A1 | 9/2003 | Suzuki et al. | 422/102 |

FOREIGN PATENT DOCUMENTS

| | | |
|---|---|---|
| JP | 2002-040031 | 2/2002 |
| JP | 2002-159285 | 6/2002 |
| JP | 2004-003888 | 1/2004 |
| WO | 2005/028611 | 3/2005 |

* cited by examiner

*Primary Examiner* — Natalia Levkovich
(74) *Attorney, Agent, or Firm* — Bacon & Thomas, PLLC (57) ABSTRACT

An analyte testing/observing apparatus includes a microplate mounting stand 10 which supports at least one of microplates 27 having a plurality of wells 27a for accommodating an analyte and microplates 28 each having a plurality of wells 28a for accommodating a reagent, and which includes a retractable shutter 20 for covering a surface of the at least one microplate mounted on the mounting stand 10. When the dispensing work is stopped, the shutter 20 is closed and lowered, so that the shutter 20 comes into contact with the surfaces of the microplates, to thereby prevent evaporation and drying of the analyte and the reagent accommodated within the wells before being dispensed.

2 Claims, 4 Drawing Sheets

MICROPLATE MOUNTING STAND, AND ANALYTE TESTING/OBSERVING APPARATUS EQUIPPED THEREWITH

TECHNICAL FIELD

The present invention relates to a microplate mounting stand, and an analyte testing/observing apparatus equipped therewith. In particular, the present invention relates to a microplate mounting stand which prevents drying of an analyte or a reagent accommodated in wells of a microplate mounted on the mounting stand before being dispensed, so as to stabilize a reaction between the analyte and the reagent, to thereby improve the accuracy of the analyte test, and to an analyte testing/observing apparatus equipped with the mounting stand.

BACKGROUND ART

Conventionally, there have been proposed and sold various types of analyte testing/observing apparatuses used for testing whether cells move in a certain direction without assistance, observing a state in which cells move in a certain direction without assistance, measuring the number of cells having moved in a certain direction without assistance, separating cells which move in a certain direction without assistance, or a like purpose. The present applicant also proposed an analyte testing/observing apparatus of such a type in WO/2005/028611 (Patent Document 1) or the like. This devised apparatus is excellent in operability, easy to operate, and enables highly accurate testing and observation of cells.

Incidentally, in such an apparatus, the following procedure is performed to cause cells (analyte) and a reagent to react with each other and test and observe the behavior of the cells. A microplate having a plurality of wells which accommodates the cells, and a microplate having a plurality of wells which accommodates the reagent are prepared. Appropriate amounts of the cells and the reagent are dispensed from the wells of the respective microplates to reaction wells within a chamber of a cell observation apparatus, and the cells and the reagent are caused to react within the reaction wells, whereby the behavior of cells is tested and observed.

Of microplates each having a plurality of wells for storing cells or a reagent, some microplates include 1500 wells each. When the cells or the reagent is dispensed from the large number of wells of such a microplate to, for example, 48-channel reaction wells, the cells or the reagent accommodated in the wells of such a microplate easily evaporates at room temperature. Therefore, it is necessary to suppress evaporation of moisture from the cells or the reagent, to thereby prevent drying of the cells or the reagent. Further, in the case where the reaction wells are formed by a large number of depressions of another microplate, it also becomes necessary to suppress evaporation of moisture from a mixture of the cells and the reagent dispensed into the reaction wells, to thereby prevent drying of the mixture.

In an analyte test apparatus disclosed in Japanese Patent Application Laid-Open (kokai) No. 2002-40031 (Patent Document 2), a plate cover having a predetermined number of openings is provided to cover, from the upper side, an area through which a microplate having a plurality of reaction wells each storing a mixture of a dispensed analyte and a dispensed reagent is transferred by a transfer apparatus. Only when the reactions within the reaction wells are tested and/or observed or the reaction wells are cleaned, the openings are opened. Thus, evaporation of moisture from the mixtures is suppressed, whereby drying of the mixtures is prevented. This structure enables obtainment of stable test results in an analyte test.

However, the plate cover of the analyte test apparatus disclosed in Patent Document 2 is fixed, and the microplate is moved. In addition, since a clearance is always preset between the microplate and the plate cover, the analyte test apparatus has a problem in that moisture easily evaporates from the mixture of the analyte and the reagent accommodated in each reaction well of the microplate, so that drying of the mixture progresses quickly. Moreover, since a lid for opening and closing the openings of the plate cover is formed of a flat plate member, a horizontally extending large space is needed so as to move the plate member to thereby open the opening portions. Therefore, the conventional analyte test apparatus cannot meet the requirement of space saving for an analyte testing/observing apparatus of such a type, which is used in a narrow space such as a laboratory.

Further, the conventional microplate mounting stand does not have means for preventing evaporation of moisture from (i.e., preventing drying of) cells or a reagent accommodated in wells of a microplate mounted on the mounting stand before being dispensed.

Patent Document 1: WO/2005/028611
Patent Document 2: Japanese Patent Application Laid-Open (kokai) No. 2002-40031

DISCLOSURE OF THE INVENTION

Problems to be Solved by the Invention

An object of the present invention is to solve the above-mentioned problems in the conventional microplate mounting stand and the conventional analyte testing/observing apparatus equipped with the microplate mounting stand, and to provide a microplate mounting stand which can suppress evaporation of moisture from an analyte or a reagent which is accommodated, before being dispensed, in a plurality of wells formed in a microplate, so as to prevent drying of the analyte or the reagent, to thereby stabilize the reaction between the analyte and the reagent and improve the accuracy of analyte test, and which can reduce a space occupied by the microplate mounting stand, as well as an analyte testing/observing apparatus equipped with the microplate mounting stand.

Means for Solving the Problems

According to the present invention, the above-described problems are solved by a microplate mounting stand as described below and an analyte testing/observing apparatus equipped with such a microplate mounting stand.

That is, the microplate mounting stand is adapted to support at least one microplate among at least one microplate having a plurality of wells for accommodating an analyte and at least one microplate having a plurality of wells for accommodating a reagent, and includes a retractable shutter for covering a surface of the at least one microplate mounted on the mounting stand.

According to the microplate mounting stand, the microplate mounted on the mounting stand and having a plurality of wells for accommodating an analyte and/or the microplate mounted on the mounting stand and having a plurality of wells for accommodating a reagent remains stationary, and the surface thereof is covered by the retractable shutter. Therefore, evaporation of moisture of the analyte which is accommodated, before being dispensed, in the plurality of wells of the corresponding microplate and/or evaporation of moisture of the reagent which is accommodated, before being dispensed, in the plurality of wells of the corresponding microplate are satisfactorily prevented, whereby drying of the analyte and/or the reagent can be satisfactorily prevented. Therefore, when the analyte is tested, the reaction between the analyte and the reagent occurs in a stable manner, whereby the accuracy of the analyte test can be improved.

Further, an analyte testing/observing apparatus according to the present invention comprises a microplate mounting stand which supports at least one microplate among at least one microplate having a plurality of wells for accommodating an analyte and at least one microplate having a plurality of wells for accommodating a reagent; a dispensing mechanism for dispensing the analyte and the reagent from the wells of the corresponding microplates to other wells or containers; and a testing/observing section for testing/observing a reaction between the analyte and the reagent, wherein the microplate mounting stand includes a retractable shutter for covering a surface of the at least one microplate mounted on the mounting stand.

According to the analyte testing/observing apparatus, the microplate mounted on the mounting stand and having a plurality of wells for accommodating an analyte and/or the microplate mounted on the mounting stand and having a plurality of wells for accommodating a reagent remains stationary, and the surface thereof is covered by the retractable shutter. Therefore, evaporation of moisture of the analyte which is accommodated, before being dispensed, in the plurality of wells of the corresponding microplate and/or evaporation of moisture of the reagent which is accommodated, before being dispensed, in the plurality of wells of the corresponding microplate are satisfactorily prevented, whereby drying of the analyte and/or the reagent can be satisfactorily prevented. Therefore, the reaction between the analyte and the reagent occurs in a stable manner, whereby the accuracy of the analyte test can be improved.

In a preferred embodiment, the shutter is configured such that it is opened and closed while being bent at an end portion of the mounting stand. By virtue of this configuration, even when the shutter is opened, the shutter does not require a space which extends horizontally in parallel with a mounting surface of the mounting stand. Therefore, the required space can be reduced. Accordingly, even when the microplate mounting stand or the analyte testing/observing apparatus is used in a narrow space such as a laboratory, the demand for space saving there can be met.

In another preferred embodiment, the mounting stand further includes a guide member for guiding opening and closing movements of the shutter, and the guide member is equipped with an elevating mechanism which elevates the guide member, when the shutter is opened or closed, so as to separate the shutter from the surface of the microplate, and lowers the guide member, when the shutter is in a closed state, so as to bring the shutter into contact with the surface of the microplate. By virtue of this configuration, the opening and closing movements of the shutter can be made smooth. Further, when the shutter is in a closed state (i.e., when dispensing of the analyte and the reagent is not performed), the shutter can cover the surface of the microplate in a state where the shutter is in contact with the surface. Therefore, evaporation of moisture from the analyte and/or the reagent can be prevented substantially completely, so that drying of the analyte and/or the reagent can be prevented substantially completely. As a result, the reaction between the analyte and the reagent occurs in a more stable manner, and the accuracy of the analyte test can be improved further.

In still another embodiment, the guide member is formed of an elongated plate-shaped member, and is provided at a central portion of the mounting stand such that the guide member extends along a direction of the opening and closing movements of the shutter. By virtue of this configuration, the guide member can equally guide the opening and closing movements of the shutter on opposite sides thereof. Therefore, the opening and closing movements of the shutter can be made smoother. In addition, the guide member enables the shutter to equally and uniformly cover the surface of the microplate on opposite sides thereof. Therefore, evaporation of moisture from the analyte and/or the reagent can be prevented more satisfactorily, so that drying of the analyte and/or the reagent can be prevented more satisfactorily. As a result, the reaction between the analyte and the reagent occurs in a more stable manner, and the accuracy of the analyte test can be improved further.

In still another embodiment, the guide member includes a plurality of rollers on its guide surface. This configuration makes the opening and closing movements of the shutter more smoother.

EFFECTS OF THE INVENTION

As described above, in the microplate mounting stand and the analyte testing/observing apparatus according to the present invention, the microplate mounted on the mounting stand and having a plurality of wells for accommodating an analyte and/or the microplate mounted on the mounting stand and having a plurality of wells for accommodating a reagent remains stationary, and the surface thereof is covered by the retractable shutter. Therefore, evaporation of moisture of the analyte which is accommodated, before being dispensed, in the plurality of wells of the corresponding microplate and/or evaporation of moisture of the reagent which is accommodated, before being dispensed, in the plurality of wells of the corresponding microplate is satisfactorily prevented, whereby drying of the analyte and/or the reagent can be satisfactorily prevented. Therefore, the reaction between the analyte and the reagent occurs in a stable manner, whereby the accuracy of the analyte test can be improved.

Further, in the case where the shutter is configured such that it is opened and closed while being bent at an end portion of the mounting stand, even when the shutter is opened, the shutter does not require a space which extends horizontally in parallel with a mounting surface of the mounting stand. Therefore, the required space can be reduced. Accordingly, even when the microplate mounting stand or the analyte testing/observing apparatus is used in a narrow space such as a laboratory, the demand for space saving there can be met.

Moreover, in the case where the mounting stand further includes a guide member for guiding opening and closing movements of the shutter, and the guide member is equipped with an elevating mechanism which elevates the guide member, when the shutter is opened or closed, so as to separate the shutter from the surface of the microplate, and lowers the guide member, when the shutter is in a closed state, so as to bring the shutter into contact with the surface of the microplate, the opening and closing movements of the shutter can be made smooth. Further, when the shutter is in a closed state (i.e., when dispensing of the analyte and the reagent is not performed), the shutter can cover the surface of the microplate in a state where the shutter is in contact with the surface. Therefore, evaporation of moisture from the analyte and/or the reagent can be prevented substantially completely, so that drying of the analyte and/or the reagent can be prevented substantially completely. As a result, the reaction between the analyte and the reagent occurs in a more stable manner, and the accuracy of the analyte test can be improved further.

Moreover, the above-described various effects can be achieved.

DESCRIPTION OF REFERENCE NUMERALS

1: analyte testing/observing apparatus; 10: mounting stand; 11: mounting stand main body; 12: support column portion; 12a: slit; 13: bottom plate; 13a: recess portion; 14: side plate; 14a: recess groove; 15: bar-shaped block; 15a: cavity; 16: positioning plate; 17: pin; 18: guide member; 19: elevating mechanism; 20: shutter; 21: reinforcement member; 22: opening-closing mechanism; 23: motor; 24: screw shaft; 25: nut member; 26: rotation receiving member; 27: microplate; 27a: well (depression); 28: microplate; 28a: well (depression); 30: dispensing mechanism; 31: nozzle portions; 40: testing/observing section; 41: testing/observing chamber; F: floor surface

BEST MODE FOR CARRYING OUT THE INVENTION

A microplate mounting stand, which supports at least one microplate among at least one microplate having a plurality of wells for accommodating an analyte and at least one microplate having a plurality of wells for accommodating a reagent, includes a retractable shutter for covering a surface of the at least one microplate mounted on the mounting stand. The shutter is opened and closed, while being curved at an end portion of the mounting stand.

Further, an analyte testing/observing apparatus comprises a microplate mounting stand which supports at least one microplate among at least one microplate having a plurality of wells for accommodating an analyte and at least one microplate having a plurality of wells for accommodating a reagent; a dispensing mechanism for dispensing the analyte and the reagent from the wells of the corresponding microplates to other wells or containers; and a testing/observing section for testing/observing a reaction between the analyte and the reagent, wherein the microplate mounting stand includes a retractable shutter for covering a surface of the at least one microplate mounted on the mounting stand. The shutter is opened and closed, while being curved at an end portion of the mounting stand.

Moreover, the mounting stand further includes a guide member for guiding opening and closing movements of the shutter, and the guide member is equipped with an elevating mechanism which elevates the guide member, when the shutter is opened or closed, so as to separate the shutter from the surface of the microplate, and lowers the guide member, when the shutter is in a closed state, so as to bring the shutter into contact with the surface of the microplate.

EMBODIMENT

Next, an embodiment of the present invention will be described.

Figure 1:
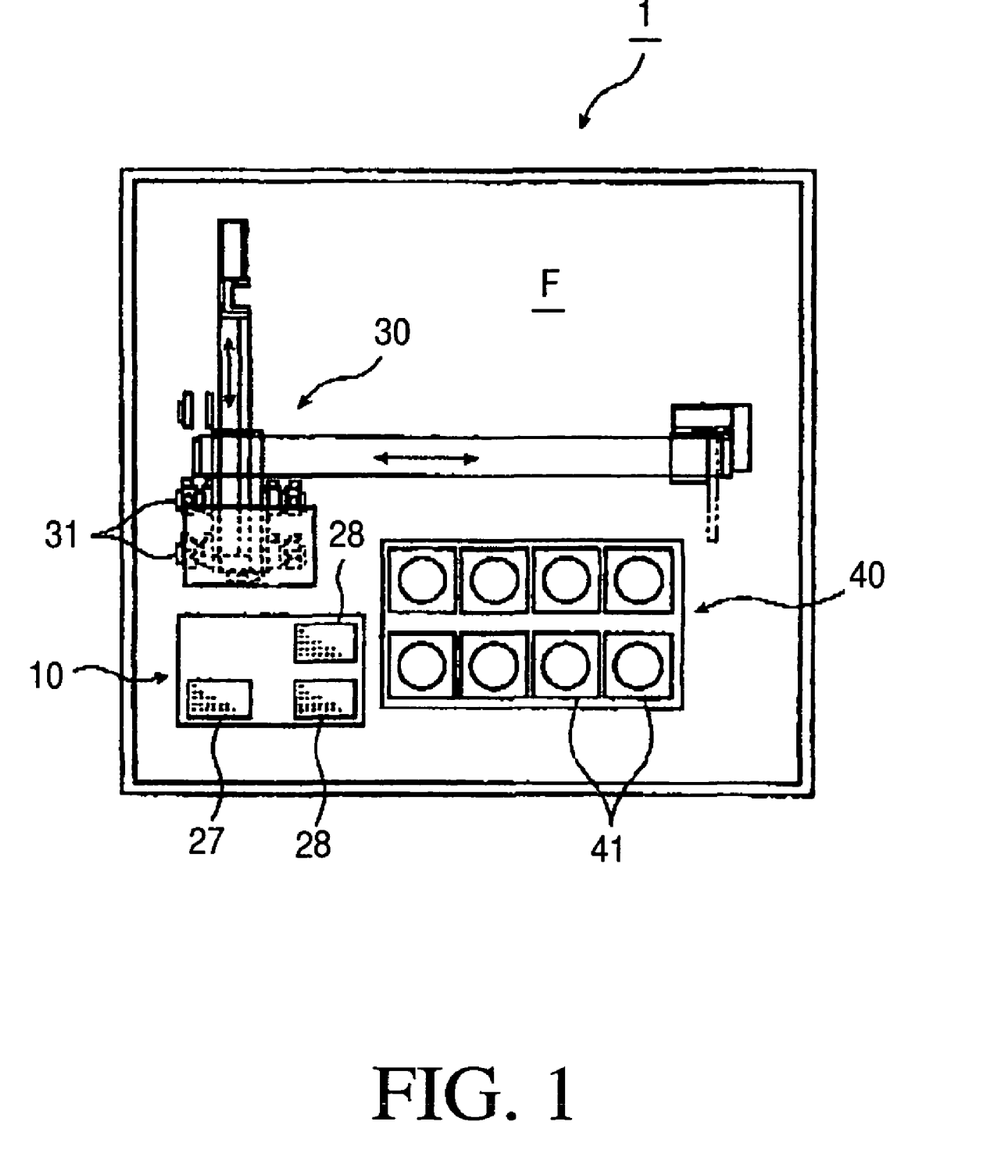
FIG. 1 is a layout view of the entirety of an analyte testing/observing apparatus according to an embodiment of the present invention.
Figure 2:
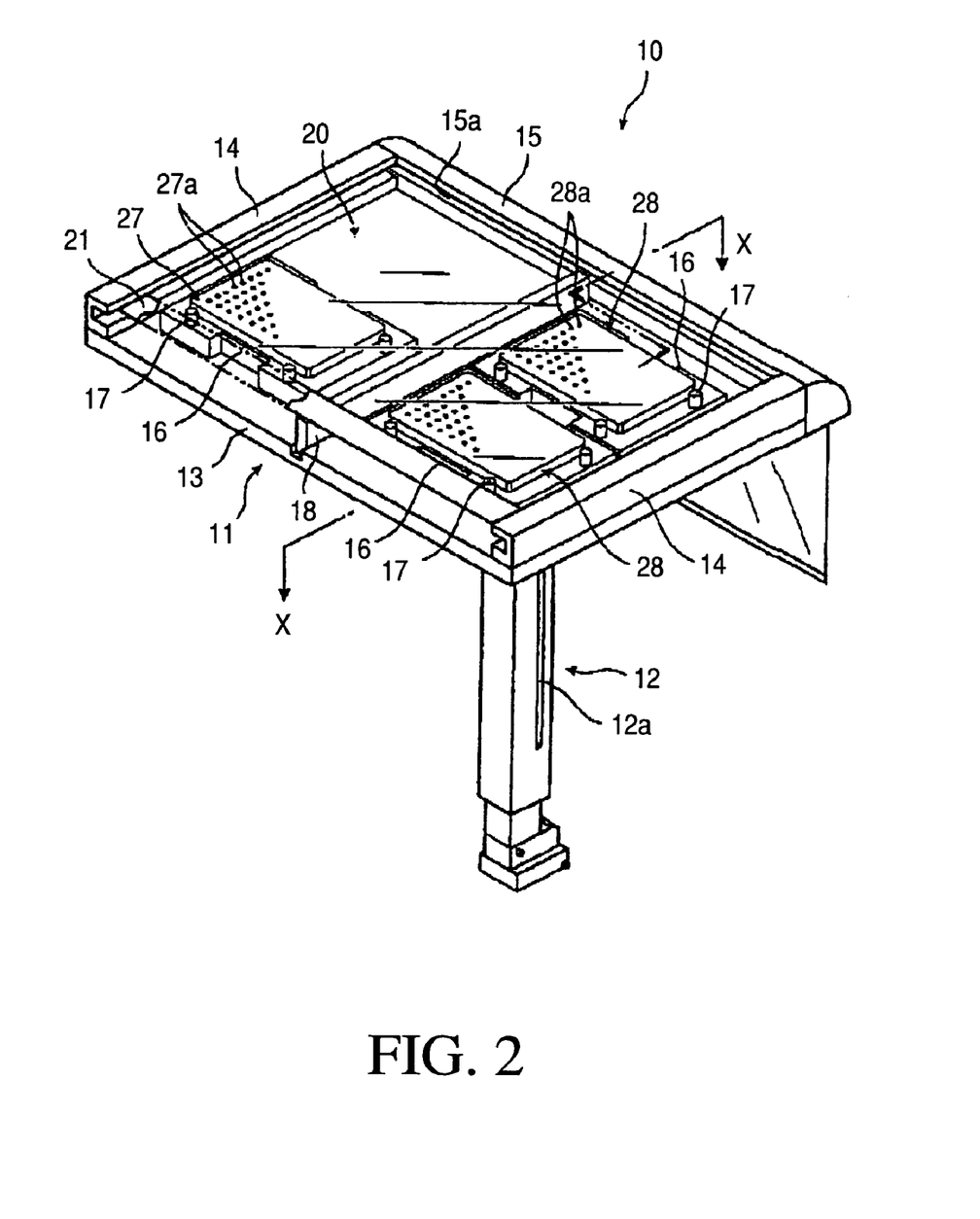
FIG. 2 is a perspective view of a mounting stand of the analyte testing/observing apparatus.
Figure 3:
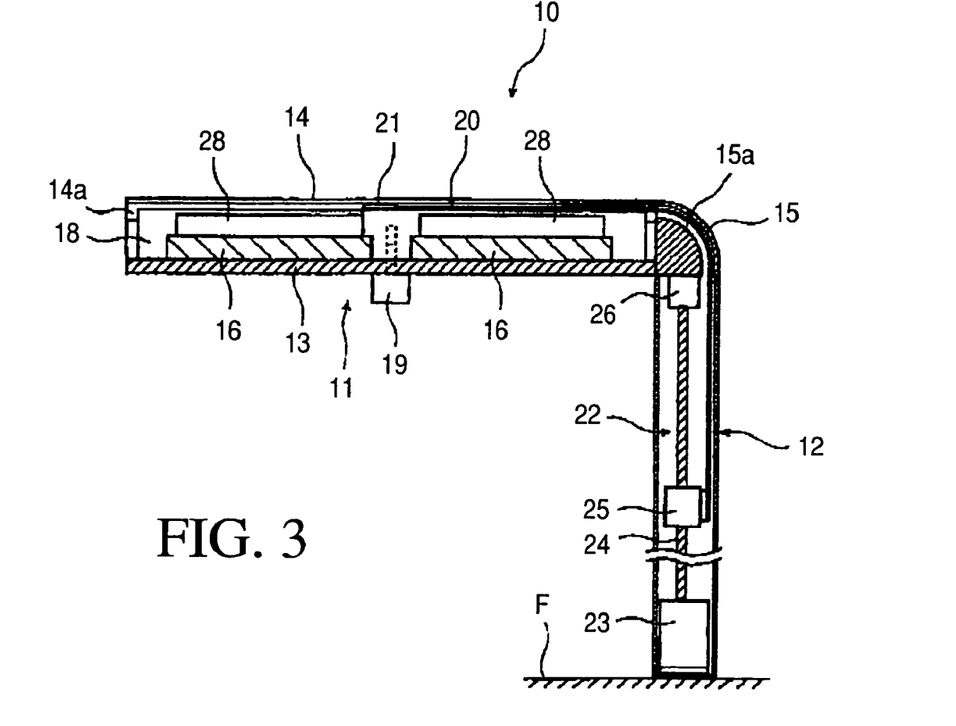
FIG. 3 is a general vertical sectional view of the mounting stand taken along line X-X of FIG. 2.
Figure 4:
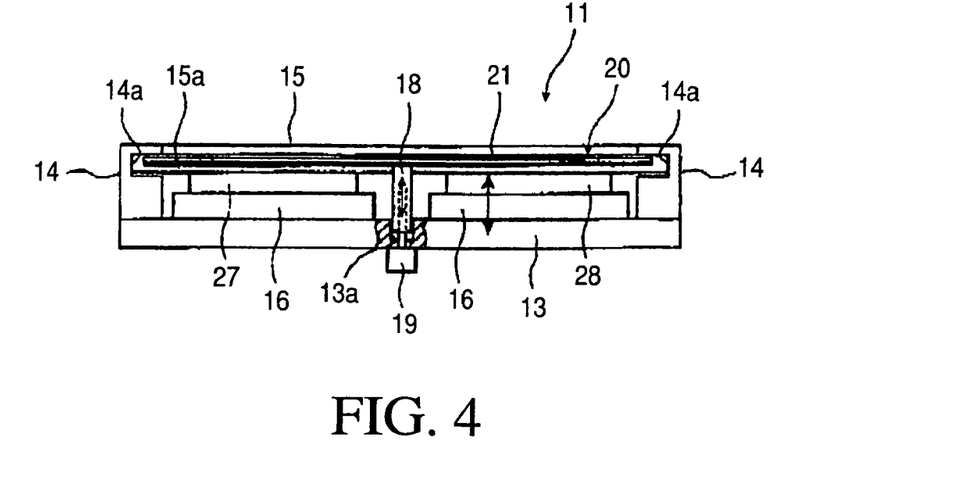
FIG. 4 is a partially broken, general front view of a main portion of the mounting stand when a shutter is in a raised position.
Figure 5:
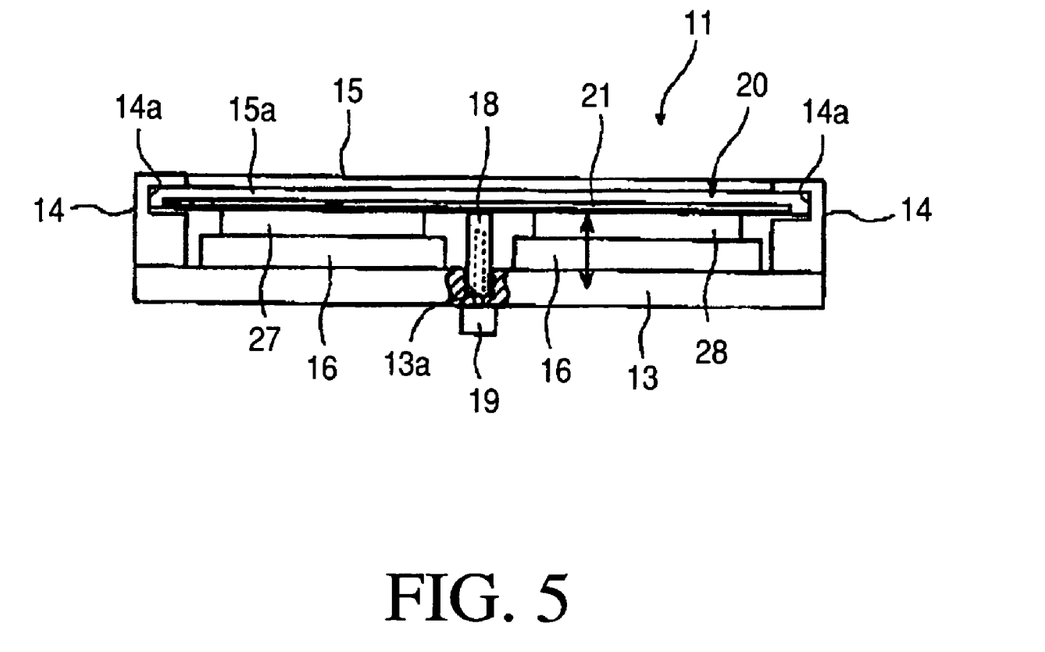
FIG. 5 is a partially broken, general front view of the main portion of the mounting stand when the shutter is in a lowered position.

FIG. 1 is a layout view of the entirety of an analyte testing/observing apparatus according to the present embodiment; FIG. 2 is a perspective view of a mounting stand of the analyte testing/observing apparatus; FIG. 3 is a general vertical sectional view of the mounting stand taken along line X-X of FIG. 2; FIG. 4 is a partially broken, general front view of a main portion of the mounting stand when a shutter is in a raised position; and FIG. 5 is a partially broken, general front view of the main portion of the mounting stand when the shutter is in a lowered position.

As shown in FIG. 1, an analyte testing/observing apparatus 1 according to the present embodiment includes a mounting stand 10, a dispensing mechanism 30, and a testing/observing section 40, which are disposed on a floor surface F. Microplates 27 and 28 are mounted on the mounting stand 10. The dispensing mechanism 30 is composed of a robot which has, at the distal end of its hand, a plurality of nozzle portions 31, which can be moved along the directions of three axes; i.e., X, Y, and Z axes. The testing/observing section 40 includes a plurality of testing/observing chambers 41. Each nozzle portion 31 includes a large number of aligned dispensing nozzles.

As shown in FIG. 2, the microplate 27 includes a plurality of wells (depressions) 27a for accommodating an analyte, and the microplate 28 includes a plurality of wells (depressions) 28a for accommodating a reagent. In the illustrated embodiment, one microplate 27 and two microplates 28 are mounted on the mounting stand 10. However, their numbers are set to desired numbers in accordance with the size of the mounting stand 10. The number of the wells 27a of the microplate 27 and the number of the wells 28a of the microplate 28 are as large as 1500.

The dispensing mechanism 30, which is composed of a robot, sucks the analyte and the reagent from the wells 27a and 28a of the corresponding microplates 27 and 28 via the dispensing nozzles, transports them to a plurality of (e.g., 48 channels) unillustrated reaction wells provided within the testing/observing chambers 41 of the testing/observing section 40, and successively injects the analyte and the reagent into the reaction wells via the dispensing nozzles. The testing/observing section 40 further includes optical means and a personal computer for testing, observing, and analyzing reactions between the analyte and the reagent occurring within the reaction wells. The reaction is tested, observed, and analyzed by use of these means.

Notably, the containers into which the analyte and the reagent are injected from the dispensing nozzles of the dispensing mechanism 30 are not limited to the reaction wells provided within the testing/observing chambers 41. The containers may be other types of wells or container-like members, depending on the testing/observing process. In these cases, each of the analyte and the reagent may be solely dispensed into these containers for a specific purpose.

Next, the structure of the mounting stand 10 will be described in detail.

As shown in FIGS. 2 and 3, the mounting stand 10 is mainly composed of a mounting stand main body 11, and a support column portion 12. The support column portion 12 stands on the floor surface F, and the mounting stand main body 11 is supported by the support column portion 12 in a cantilever fashion at a center portion of the rear side (extending in an upper right portion of FIG. 2) of the mounting stand main body 11. The interior of the support column portion 12 is hollow, and an opening-closing mechanism 22 which opens and closes a shutter 20 to be described later is accommodated there.

The mounting stand main body 11 includes a bottom plate 13, which has a rectangular shape as viewed from above and whose three sides, excluding the front side (a left lower side in FIG. 2), are surrounded by two side plates (hereinafter may be referred to as the "left and right side plates") 14 extending along the left and right sides of the bottom plate 13, and a single bar-shaped block 15 extending along the rear side (a right upper side in FIG. 2). Thus, the mounting stand main body 11 assumes the form of a shallow container which is open at the front side and is open upward. Positioning plates 16, which support and position the microplates 27 and 28, are disposed on the bottom plate 13 while being aligned in the front-rear direction and the right-left direction. Three pins 17 for positioning the microplate 27 or 28 are studded on the upper surface of each positioning plate 16 along the peripheral edge thereof. Of the three pins 17 on each positioning plate 16, two pins come into contact with one side of the microplate 27 or 28, and the remaining one pin comes into contact with another side thereof perpendicular to the one side. Thus, the three pins 17 position the microplate 27 or 28 at a predetermined position on the positioning plate 16. The bar-shaped block 15 has a generally quarter-circular transverse cross section.

As described above, an analyte is accommodated in the wells 27a of the microplate 27, and a reagent is accommodated in the wells 28a of the microplate 28. If the microplates 27 and 28 are placed on the mounting stand main body 11 without being covered, the analyte and the reagent come into contact with the ambient air, and moisture evaporates from the analyte and the reagent. Therefore, drying of the analyte and the reagent cannot be avoided. In the present embodiment, the mounting table 10 includes the retractable shutter 20. When necessary, the shutter 20 generally completely covers the surfaces of the microplates 27 and 28, whereby the above-described evaporation of moisture from the analyte and the reagent and drying of the analyte and the reagent can be avoided.

Next, the structure of the retractable shutter 20 and the structure for opening and closing the shutter 20 will be described in detail.

As is better shown in FIGS. 4 and 5, a recess groove 14a is formed on the inner side surface of each of the two side plates 14 extending along the left and right sides of the bottom plate 13 of the mounting stand main body 11. A cavity 15a is formed in the single bar-shaped block 15 extending along the rear side of the bottom plate 13 of the mounting stand main body 11. The cavity 15a extends along the longitudinal direction of the block 15 and has a generally arcuate-strip-like transverse cross section corresponding to a quarter of a circle. An imaginary circle corresponding to the arcuate-strip-like transverse cross section of the cavity 15a is concentric with that of an imaginary circle corresponding to the quarter-circular transverse cross section of the bar-shaped block 15. Further, at opposite end portions of the cavity 15a with respect to the longitudinal direction thereof, one end of the cavity 15a as viewed in a transverse cross section thereof communicates with the recess grooves 14a of the left and right side plates 14. Therefore, the cavity 15a and the recess grooves 14a of the left and right side plates 14 communicate with each other.

The shutter 20, which assumes a rectangular shape as viewed from above and is formed of a thin plate-shaped flexible member (thickness: about 0.2 mm), is placed in the space formed by the cavity 15a and the recess grooves 14a of the left and right side plates 14 such that the shutter 20 can be advanced and retracted along the longitudinal direction of the recess grooves 14a. A thin reinforcement member 21 is bonded to the upper surface of the shutter 20 at a front end thereof. The reinforcement member 21 serves as a head portion for advancing and retracting movements (open and close movements) of the shutter 20, and imparts rigidity to the shutter 20. A rear end portion of the shutter 20 extends downward from the other end of the cavity 15a as viewed in a transverse cross section thereof, and is connected to the opening-closing mechanism 22 accommodated within the support column portion 12.

When the opening-closing mechanism 22 is operated, the shutter 20 advances and retracts in the front-rear direction of the mounting stand main body 11 along the left and right recess grooves 14a, while curving and deforming in the cavity 15a provided at the rear end portion of the mounting stand main body 11. When the head portion of the shutter 20 advances to the vicinity of the front end of the mounting stand main body 11, the shutter 20 covers the surfaces of the microplates 27 and 28 so as to suppress evaporation of moisture from the analyte and the reagent accommodated in the wells 27a and 28a of the microplates 27 and 28, to thereby prevent drying of the analyte and the reagent. When the head portion of the shutter 20 moves backward (retracts) to the rear end of the mounting stand main body 11, the surfaces of all the microplates 27 and 28 are exposed. Notably, a slit 12a is formed in the support column portion 12 along the longitudinal direction thereof in order to enable the shutter 20, which is expanded in the right-left direction, to move in the vertical direction.

The opening-closing mechanism 22 is configured as follows.

A motor 23 is fixedly disposed at the lower end of the interior of the support column portion 12, and a nut member 25 is in screw engagement with a screw shaft 24 connected to a rotation shaft of the motor 23. Therefore, when the motor 23 is activated, the screw shaft 24 rotates, whereby the nut member 25 moves vertically along the screw shaft 24. As a result, the shutter 20 advances and retracts in the front-rear direction of the mounting stand main body 11 along the left and right recess grooves 14a, while curving and deforming in the cavity 15a, whereby the shutter 20 covers or uncovers the surfaces of the microplates 27 and 28 mounted on the mounting stand main body 11. An upper end portion of the screw shaft 24 is rotatably supported by a rotation receiving member 26, which is fixed to the lower surface of the bar-shaped block 15 and which assumes the form of a short circular column.

The mounting stand main body 11 further includes a guide member 18 for guiding the opening and closing movements (advancing and retracting movements) of the shutter 20.

As shown in FIGS. 2 to 5, the guide member 18 is composed of an elongated plate-shaped member, and is provided at a central portion of the mounting stand main body 11 such that it extends along the direction of the opening and closing movements (advancing and retracting movements) of the shutter 20. The guide member 18 is equipped with an elevating mechanism 19, which includes a motor or the like as a drive source. Through operation of the elevating mechanism 19, the guide member 18 is elevated and lowered. The elevating mechanism 19 is attached to the lower surface of the bottom plate 13 of the mounting stand main body 11.

The elevating and lowering of the guide member 18 will be described specifically. When the shutter 20 is opened or closed, the guide member 18 is raised so as to separate the shutter 20 from the surfaces of the microplates 27 and 28, to thereby make the opening and closing operations of the shutter 20 smooth. Further, when the shutter 20 remains stationary after having covered the surfaces of the microplates 27 and 28, the guide member 18 is lowered so as to bring the shutter 20 in contact with the surfaces of the microplates 27 and 28. As a result, the openings of the wells 27a and 28a of the microplates 27 and 28 are closed substantially completely, whereby the analyte and the reagent accommodated in the wells 27a and 28a are prevented from coming into contact with the ambient air. As a result, evaporation of moisture from the analyte and the reagent can be prevented substantially completely, so that drying of the analyte and the reagent can be prevented substantially completely. A recess 13a is formed in the bottom plate 13 of the mounting stand main body 11 so as to allow the elevating and lowering movements of the guide member 18.

Notably, preferably, the guide member 18 has a plurality of rollers along its guide surfaces. In this case, the guiding action of the guide member 18 is enhanced, whereby the opening and closing operations of the shutter 20 can be made smoother. Further, in a case where the width of the mounting stand main body 11 with respect to the left-right direction is increased and the number of rows of the microplates 27 and 28 in the left-right direction is increased, preferably, the guide member 18 is disposed in parallel with the left and right recess grooves 14a at a plurality of positions corresponding to the increased number of rows of the microplates 27 and 28 such that the guide members equally divide the width (in the right-left direction) of the mounting stand main body 11. This configuration enables the shutter 20 to come into contact with the surfaces of the microplates 27 and 28 generally uniformly at all positions. This configuration is preferred so as to prevent drying of the analyte and the reagent.

By virtue of the above-described configuration, the microplate mounting stand 10 of the present embodiment and the analyte testing/observing apparatus 1 equipped with the microplate mounting stand 10 can achieve the following effects. The microplate 27 mounted on the mounting stand 10 and having the plurality of wells 27a for accommodating the analyte and the microplate 28 mounted on the mounting stand 10 and having the plurality of wells 28a for accommodating the reagent remain stationary, and their surfaces are covered by the retractable shutter 20. Therefore, evaporation of moisture of the analyte and moisture of the reagent which are accommodated, before being dispensed, in the plurality of wells 27a and 28a of the corresponding microplates 27 and 28 are satisfactorily prevented, whereby drying of the analyte and the reagent can be satisfactorily prevented. Therefore, the reaction between the analyte and the reagent occurs in a stable manner, whereby the accuracy of the analyte test can be improved.

Further, the mounting stand 10 includes the guide member 18 for guiding opening and closing movements of the shutter 20. The guide member 18 is equipped with the elevating mechanism 19 which elevates the guide member 18, when the shutter 20 is opened or closed, so as to separate the shutter 20 from the surfaces of the microplates 27 and 28, and lowers the guide member 18, when the shutter 20 is in a closed state, so as to bring the shutter 20 into contact with the surfaces of the microplates 27 and 28. Therefore, the opening and closing movements of the shutter 20 can be made smooth. Further, when the shutter 20 is in a closed state (i.e., when dispensing of the analyte and the reagent is not performed), the shutter 20 can cover the surfaces of the microplates 27 and 28 in a substantially sealed state in which the shutter 20 is in contact with the surfaces. Therefore, evaporation of moisture of the analyte and the reagent can be prevented substantially completely, so that drying of the analyte and the reagent can be prevented substantially completely. As a result, the reaction between the analyte and the reagent occurs in a more stable manner, and the accuracy of the analyte test can be improved further.

Further, the guide member 18 is formed of an elongated plate-shaped member, and is provided at a central portion of the mounting stand main body 11 such that the guide member 18 extends along a direction of the opening and closing movements of the shutter 20. By virtue of this configuration, the guide member 18 can equally guide the opening and closing movements of the shutter 20 on opposite sides thereof. Therefore, the opening and closing movements of the shutter 20 can be made smoother. In addition, the guide member 18 enables the shutter 20 to equally and uniformly cover the surfaces of the microplates 27 and 28 on opposite sides thereof. Therefore, evaporation of moisture of the analyte and the reagent can be prevented more satisfactorily, so that drying of the analyte and the reagent can be prevented more satisfactorily. As a result, the reaction between the analyte and the reagent occurs in a more stable manner, and the accuracy of the analyte test can be improved further.

The shutter 20 is configured such that it is opened and closed while being bent in the cavity 15a at the end of the mounting stand main body 11. Therefore, even when the shutter 20 is opened (retracted), the shutter 20 does not require a space which extends horizontally in parallel with a mounting surface of the mounting stand main body 11. Therefore, the required space can be reduced. Accordingly, even when the microplate mounting stand 10 or the analyte testing/observing apparatus 1 equipped with the mounting stand 10 is used in a narrow space such as a laboratory, the demand for space saving there can be met.

Further, the above-described various effects can be achieved.

The present invention is not limited to the above-described embodiment. Numerous modifications and variations of the present invention are possible without departing from the gist of the invention.

For example, in the above-described embodiment, the cavity 15a is formed by removing an interior portion of the bar-shaped block 15. However, the method of forming the cavity 15a is not limited thereto. For example, the bar-shaped block 15 may be fabricated by means of assembling a plurality of segments each having a partial contour shape of the cavity 15a, whereby the cavity 15a is formed.

The invention claimed is:

1. A microplate mounting stand for mounting thereon at least one microplate having a plurality of wells, the mounting stand comprising a flexible sheet shutter for covering a surface of the at least one microplate mounted on the mounting stand and an opening-closing mechanism for moving the shutter between a position where the shutter covers the at least one microplate and a position where the at least one microplate is uncovered; and opposing side plates with respective guide grooves which receive opposing edges of the shutter and guide the shutter in horizontal movement relative to the at least one mounted microplate and a member extending transversely to the side plates and having a guide groove with an arcuate surface which receives and bends the shutter from horizontal to vertical.

2. An analyte testing/observing apparatus comprising:
a microplate mounting stand which supports at least one microplate having a plurality of wells;
a dispensing mechanism for transferring analyte and the reagent from the wells of the at least one microplate to other wells or containers; and
a testing/observing section for testing/observing a reaction between the analyte and the reagent,
wherein the microplate mounting stand includes:
a flexible sheet shutter for covering a surface of the at least one microplate mounted on the mounting stand and an opening-closing mechanism for moving the shutter between a closed position where the shutter covers the at least one microplate and an open position where the at least one microplate is uncovered; and
opposing side plates with respective guide grooves which receive opposing edges of the shutter and guide the shutter in horizontal movement relative to the at least one mounted microplate and a member extending transversely to the side plates and having a guide groove with an arcuate surface which receives and bends the shutter from horizontal to vertical.

* * * * *

UNITED STATES PATENT AND TRADEMARK OFFICE
CERTIFICATE OF CORRECTION

| | | |
|---|---|---|
| PATENT NO. | : 8,137,643 B2 | Page 1 of 1 |
| APPLICATION NO. | : 12/227021 | |
| DATED | : March 20, 2012 | |
| INVENTOR(S) | : Kazuyuki Matsumura | |

It is certified that error appears in the above-identified patent and that said Letters Patent is hereby corrected as shown below:

Title page, Item (57) ABSTRACT
    line 8 of ABSTRACT, after the word "dispensing" delete the word "work"

Column 11, claim 2, line 4, after the word "and" delete the word "the"

Signed and Sealed this
Eighth Day of May, 2012

David J. Kappos
*Director of the United States Patent and Trademark Office*